(12) United States Patent
Breuer et al.

(10) Patent No.: US 7,345,033 B2
(45) Date of Patent: Mar. 18, 2008

(54) CARBAMOYL- AND THIOCARBAMOYL-PHOSPHONATES AND PHARMACEUTICAL COMPOSITIONS COMPRISING THEM

(75) Inventors: Eli Breuer, Jerusalem (IL); Reuven Reich, Rehovot (IL); Gershon Golomb, Efrat (IL); Yiffat Katz, Neve Daniel (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 74 days.

(21) Appl. No.: 11/244,405

(22) Filed: Oct. 6, 2005

(65) Prior Publication Data

US 2006/0111328 A1    May 25, 2006

Related U.S. Application Data

(63) Continuation-in-part of application No. PCT/IL2004/000302, filed on Apr. 1, 2004.

(60) Provisional application No. 60/460,408, filed on Apr. 7, 2003.

(51) Int. Cl.
*A61K 31/66* (2006.01)
*C07F 9/22* (2006.01)

(52) U.S. Cl. ........................ 514/114; 562/15

(58) Field of Classification Search ........... 514/114; 562/15
See application file for complete search history.

(56) References Cited

FOREIGN PATENT DOCUMENTS

WO    WO 01/26661    *    4/2001    ................. 514/114
WO    WO 01/26661 A1    4/2001

OTHER PUBLICATIONS

Whittaker et al., "Design and Therapeutic Application of Matrix Metalloproteinase Inhibitors", *Chem. Rev.* vol. 99, pp. 2735-2776, 1999.

Chen et al., "Long-Chain Functional Bisphosphonates: Synthesis, Anticalcification, and Antiresorption Activity", *Heteroatom Chemistry*, vol. 11, No. 7, pp. 470-479, 2000.
Salomon et al., "Efficient and Selective Dealkylation of Phosphonate Diisopropyl Esters Using Me3SiBr", *Tetrahedron Letters*, vol. 36, No. 37, pp. 6759-6760, 1995.
Cava et al., "Thionation Reactions of Lawesson's Reagents", *Tetrahedron*, vol. 41, No. 22, pp. 5061-5087, 1985.
Ferenc Fulop, "The Chemistry of 2-Aminocycloalkanecarboxylic Acids", *Chem. Rev.* vol. 101, pp. 2181-2204, 2001.
Makomo et al., "Catalyzed Amination of Dithioacid Sodium Salts: A One Pot Synthesis of α-Phosphonothioamides", *Phosphorous, Sulfur, and Silicon*, vol. 80, pp. 31-36, 1993.

* cited by examiner

*Primary Examiner*—Rebecca Anderson
*Assistant Examiner*—Yong Chu
(74) *Attorney, Agent, or Firm*—Browdy and Neimark

(57) ABSTRACT

The present invention provides a compound of the following formula I:

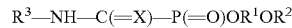

$R^3$—NH—C(=X)—P(=O)$OR^1OR^2$ including pharmaceutically acceptable salts, solvates, hydrates and polymorphs of the compounds of formula I, as well as geometrical isomers and optically active forms of the compounds of formula I and pharmaceutically acceptable salts, solvates, hydrates and polymorphs of said isomers and forms,
wherein
$R^1$ and $R^2$ may be the same or different and are each selected from hydrogen, acyloxyalkyl and aryl or $R^1$ and $R^2$ may form together with the oxygen and phosphorus atoms a dioxaphosphacycloalkane ring;
X is O or S; and
$R^3$ is selected, when X is O, from bicycloalkyl, cycloalkylalkyl and substituted cycloalkyl by at least one of alkyl, amino, amidino and guanidino; and $R^3$ is selected, when X is S, from bicycloalkyl, cycloalkylalkyl and cycloalkyl optionally substituted by at least one of alkyl, amino, amidino and guanidino; with the proviso that:
when X is O, $R^3$ is not cyclohexylmethyl, and
when X is S, $R^3$ is not cyclohexyl.

The invention further provides pharmaceutical compositions comprising the above compounds and their use in medicine.

7 Claims, 6 Drawing Sheets

CARBAMOYL- AND THIOCARBAMOYL-PHOSPHONATES AND PHARMACEUTICAL COMPOSITIONS COMPRISING THEM

FIELD OF THE INVENTION

This invention relates to certain novel compounds, to processes for preparing such compounds, to pharmaceutical compositions comprising them and to the use of such compounds and compositions in medicine.

BACKGROUND OF THE INVENTION

Inhibition of matrix metalloproteinases (MMPs) as an approach to treat diseases such as cancer, arthritis, restenosis or multiple sclerosis is now an area of intense interest within the pharmaceutical industry (see Whittaker, M., Floyd, C. D.; Brown, P.; Gearing, A. J. H. Chem. Rev. 1999, 99, 2735-2776).

MMPs are a family of zinc-containing calcium dependent enzymes, including stromelysins, collagenases and gelatinases. Over twenty MMPs have been identified. MMPs are capable of degrading and remodeling many proteinaceous components of the extracellular matrix in both physiological and pathological conditions. Misregulation and overexpression of MMPs is believed to be a major factor in a number of disease states, most of them characterized by unwanted degradation of connective tissue. These include rheumatoid arthritis, tumor invasion, metastasis, angiogenesis, multiple sclerosis, periodontal disease, coronary artery disease, restenosis, congestive heart failure, abnormal wound healing, bone matrix degradation, osteoporosis, liver cirrhosis, cerebral ischemia, meningitis and others. Tumor cell invasiveness has been shown to be MMP-dependent, and MMP inhibitors have been shown to prevent tumor cell invasion in vitro and in vivo.

Coronary atherosclerosis and its clinical progression continue to be the leading cause of mortality in the Western society. Percutaneous transluminal coronary angioplasty (PTCA) has become a mainstay in the treatment of ischemic heart disease with an estimated over 1 million procedures performed annually in the US and Europe. PTCA procedures include balloon dilation, excisional atheroctomy, endoluminal stenting and laser ablation. Despite significant advances in reducing the acute complications of percutaneous revascularization procedures with pre-medications and better techniques, chronic restenosis of dilated lesions remains a serious and frequent problem, occurring in 20% to 30% of patients.

Some carbamoylphosphonate derivatives were described in WO 01/26661 as capable of inhibiting MMPs.

SUMMARY OF THE INVENTION

In accordance with the present invention, it has been surprisingly found that a specific group of compounds from the compounds of formula I of WO 01/26661 have improved selectivity of action and are therefore of particular use in the prevention, treatment and/or prophylaxis of disease states or conditions related to matrix metalloproteinases (MMPs). More specifically, the new compounds of the present invention have carbamoyl- or thiocarbamoylphosphonate structures and are considered to be useful in the prevention, treatment and/or prophylaxis of various disease states or conditions related to MMPs for example cancer, arthritis, restenosis, autoimmune diseases, inflammation-associated diseases, osteoarthritis, osteoporosis, asthma, chronic obstructive pulmonary disease (COPD), periodontitis, atherosclerosis, psoriasis, corneal, epidermal and gastric ulcerations, cardiovascular diseases, pulmonary disease, post-ischemic reperfusion injury, congestive heart failure, hyperoxic alveolar injury and acute phase responses, septic shock and hemodynamic shock.

The autoimmune disease may be rheumatoid arthritis, multiple sclerosis, Crohn's disease or colitis.

Accordingly, the present invention provides according to a first aspect thereof novel carbamoylphosphonates and thiocarbamoylphosphonates of the following formula I:

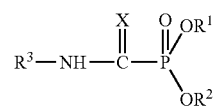

including pharmaceutically acceptable salts, solvates, hydrates and polymorphs of the compounds of formula I, as well as geometrical isomers and optically active forms of the compounds of formula I and pharmaceutically acceptable salts, solvates, hydrates and polymorphs of said isomers and forms, wherein $R^1$ and $R^2$ may be the same or different and are each selected from hydrogen, acyloxyalkyl and aryl, or $R^1$ and $R^2$ may form together with the oxygen and phosphorus atoms a dioxaphosphacycloalkane ring;

X is O or S;

$R^3$ is selected, when X is O, from bicycloalkyl, cycloalkylalkyl and substituted cycloalkyl by at least one of alkyl, amino, amidino and guanidino; and $R^3$ is selected, when X is S, from bicycloalkyl, cycloalkylalkyl and cycloalkyl optionally substituted by at least one of alkyl, amino, amidino and guanidino; with the proviso that:

when X is O, $R^3$ is not cyclohexylmethyl, and when X is S, $R^3$ is not cyclohexyl.

The compounds of the invention may have asymmetric carbon atoms and therefore they can exist either as racemic mixtures or as individual optically active forms (enantiomers or diastereomers). Accordingly, the present invention also includes within its scope all the possible isomers and their mixtures of the compounds of the invention. In a similar manner, the compounds of the present invention may exist, when crystalline, in polymorphic forms. Accordingly, the present invention also includes within its scope all the possible polymorphs of the compounds of formula I.

The term "alkyl", when it appears alone or as part of the cycloalkylalkyl group, covers also alkylene groups and preferably consists of 1-6 carbon atoms. When the alkyl radical consists of 3 or more carbons, it may be linear or branched. In addition, the ring-size of cycloalkyl groups is preferably of 3-8 atoms and the bicycloalkyl skeleton consist preferably of 6-10 atoms. The terms "cycloalkyl" and "bicycloalkyl" cover also cycloalkylene and bicycloalkylene moieties which comprise at least one unsaturated bond. It is also to be mentioned that the terms "bicycloalkyl" and "cycloalkylalkyl" embrace also the option of having these groups substituted by at least one of the following: alkyl, amino, amidino and guanidino, while the terms "amino", "amidino" and "guanidino" cover both substituted and unsubstituted such radicals, where the substituents are preferably alkyl groups. Thus, for example, a substituted amino group would amount into a secondary or tertiary amino group substituent.

Preferably, when X is O in the above formula I, $R^3$ is selected from the group consisting of substituted cycloalkyl and bicycloalkyl. More preferably $R^3$ is selected from substituted cyclohexyl and norbornyl. Even more preferably $R^3$ is selected from 2-aminocyclohexyl, cyclohexylethyl and norbornyl. When X is S in the above formula I, $R^3$ is preferably substituted cycloalkyl, more preferably substituted cyclohexyl and even more preferably cyclohexylalkyl.

More specifically, favorable compounds in accordance with the invention are those of formula I, wherein X is O and $R^3$ is selected from (R)-1-cyclohexylethyl, endo-2-norbornyl and cis-2-aminocyclohexyl. An additional favorable compound is a compound of formula I wherein X is S and $R^3$ is cyclohexylmethyl.

Further aspects of the present invention are the use of the new compounds of formula I above in the preparation of medicaments and pharmaceutical compositions comprising them as active ingredients.

The present invention also provides a method of treating mammals having disease states alleviated by the inhibition of matrix metalloproteinases, comprising administering to an individual in need an effective amount of a compound of the general formula I or a pharmaceutically acceptable salt thereof.

The term "effective amount" is meant to denote an amount of the active ingredient (the phosphonate of formula I above, or a pharmaceutically acceptable salt, hydrate, solvate or polymorph of the compound of formula I, as well as geometrical isomers and optically active forms of the compound of formula I and pharmaceutically acceptable salt, solvate, hydrate and polymorph of said isomers or forms) which is effective in achieving the desired therapeutic result. The effective amount may depend on a number of factors including: the dosage form, the age group of the treated individual and his weight, the mode of administration of the active ingredient, the type of carrier being used (e.g. whether it is a carrier that rapidly releases the active ingredient or a carrier that releases it over a period of time), as well as on various other factors as known per se. The artisan, by routine type experimentation should have no substantial difficulties in determining the effective amount in each case.

BRIEF DESCRIPTION OF THE DRAWINGS

In order to understand the invention and to see how it may be carried out in practice, preferred embodiments will now be described, by way of non-limiting example only, with reference to the accompanying drawings, in which.

DETAILED DESCRIPTION OF THE INVENTION

Figure 1:
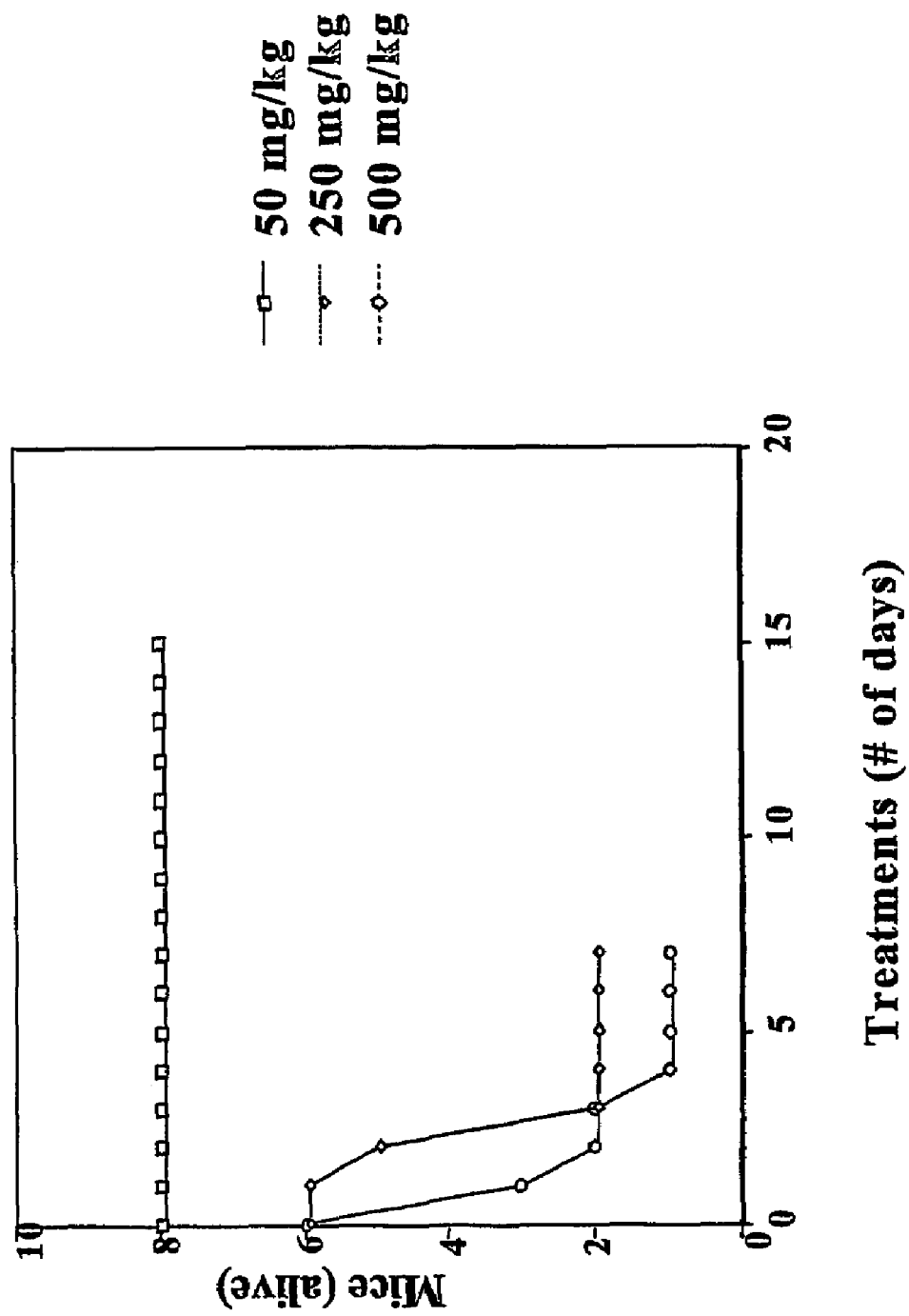
FIG. 1 is a graph showing the toxicity of compound 1 in mice at three different doses.

In accordance with the present invention, it has been surprisingly found that several specific carbamoyl- or thiocarbamoylphosphonates have remarkable biological properties connected to their inhibitory effects on matrix metalloproteinases (MMP). These properties include, inter alia: reduced toxicity; improved oral bioavailability; in vivo ability to prevent the dissemination of cancer metastases in lungs; in vivo ability to prevent the dissemination of metastases in prostate cancer, and in vivo ability to prevent restenosis.

The new compounds of the invention have the following formula I:

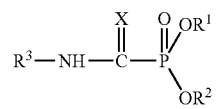

including pharmaceutically acceptable salts, hydrates, solvates and polymorphs of the compounds of formula I, as well as geometrical isomers and optically active forms of the compounds of formula I and pharmaceutically acceptable salts, solvates, hydrates and polymorphs of said isomers and forms, wherein $R^1$ and $R^2$ may be the same or different and are each selected from hydrogen, acyloxyalkyl and aryl, or $R^1$ and $R^2$ may form together with the oxygen and phosphorus atoms a dioxaphosphacycloalkane ring;

X is O or S; and $R^3$ is selected, when X is O, from bicycloalkyl, cycloalkylalkyl and substituted cycloalkyl by at least one of alkyl, amino, amidino and guanidino; and $R^3$ is selected, when X is S, from bicycloalkyl, cycloalkylalkyl and cycloalkyl optionally substituted by at least one of alkyl, amino, amidino and guanidino; with the proviso that:

when X is O, $R^3$ is not cyclohexylmethyl, and when X is S, $R^3$ is not cyclohexyl.

It will be appreciated that the present invention encompasses all of the isomeric forms of the compounds of formula I and the pharmaceutically acceptable salts, hydrates, solvates and polymorphs thereof, including any optically active forms thereof, whether as individual isomers or as racemic mixtures.

The compounds of the invention may generally be synthesized by using methods known in the art: C. J. Salomon and E. Breuer, Facile "One-Pot" Preparation of Phosphonothiolformates—A Convenient Approach to Carbamoylphosphonates, *Synlett*, 2000, 815-6.R. Chen, A. Schlossman, E. Breuer, G. Hägele, C. Tillmann, J. M. Van Gelder, and G.

Golomb Long-Chain Functional Bisphosphonates—Synthesis, Anticalcification and Antiresorption Activity, *Heteroatom Chemistry*, 2000, 11, 470-479. C. J. Salomon and E. Breuer, Efficient and Selective Dealkylation of Phosphonate Diisopropyl Esters Using Me₃SiBr, *Tetrahedron Letters*, 1995, 36, 6759-6760. M. P. Cava and M. I. Levinson, Thionation reactions of Lawesson's reagents, *Tetrahedron*, 1985, 41, 5061-5087. A typical procedure would include reacting an amine with trialkyl phosphonothiolformate to form an N-substituted carbamoylphosphonate diester, followed by bromotrimethylsilane mediated dealkylation. Alternatively, an N-substituted carbamoylphosphonate diester can be synthesized by the base-catalyzed addition of a dialkyl phosphite to an isocyanate. Thiocarbamoylphosphonate diesters are synthesized by heating a carbamoylphosphonate diester with 2,4-bis(4-methoxyphenyl)-1,3-dithia-2,4-diphosphetane-2,4-disulfide also known as Lawesson's reagent.

The optically active starting materials for the preparation of the pure enantiomers of cis-2-aminocyclohexanecarboxylic acid, the analogous cis-2-aminocyclobutanecarboxylic acid, and cis-2-aminocyclopentanecarboxylic acid may be obtained by resolution or enantioselective synthetic methods described in the article by F. Fülöp, Chem. Rev. 2001, 101, 2181.

The following scheme shows the preparation of (1R,2S)-2-aminocyclohexylcarbamoylphosphonic acid and its N-dimethylamino derivative.

epidermal and gastric ulcerations, cardiovascular diseases, pulmonary disease, post-ischemic reperfusion injury, congestive heart failure, hyperoxic alveolar injury and acute phase responses, septic shock and hemodynamic shock.

Preferably, the disease states are selected from cancer, metastasis, angiogenesis, arthritis, restenosis and wound healing and the autoimmune disease is selected from rheumatoid arthritis, multiple sclerosis, Crohn's disease and colitis.

Table 1 below shows a summary of the biological effects of selected novel carbamoylphosphonates (compounds 8-11) in comparison with those of known carbamoylphosphonic acids described in WO 01/26661 (compounds 1-7) of the same Applicants, in order to show the surprising improved characteristics.

For example, cyclohexylmethylthiocarbamoylphosphonic acid (compound 8 in Table 1) shows improved oral bioavailability in comparison to cyclohexylmethyl carbamoylphosphonic acid (compound 5 in Table 1, disclosed in WO 01/26661). The improvement in the oral bioavailability could not have been predicted, especially in view of the biological data obtained for compounds 1 and 2 in Table 1, that possess similar structural differences as compounds 5 and 8.

(R)-1-cyclohexylethylcarbamoylphosphonic acid (compound 9 in Table 1) may also be compared with cyclohexylmethylcarbamoylphosphonic acid (compound 5 in Table 1),

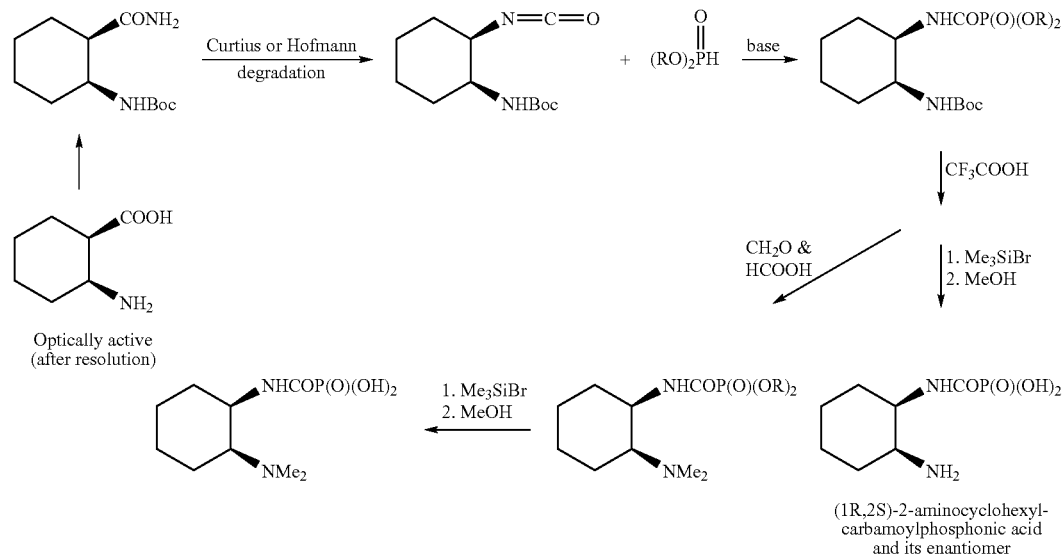

The novel compounds of the present invention are of particular use in the prevention, treatment and/or prophylaxis of disease states or conditions related to matrix metalloproteinases (MMPs). More specifically, the new compounds of the present invention are considered to be useful in the prevention, treatment and/or prophylaxis of disease states selected from cancer, arthritis, restenosis, autoimmune diseases, inflammation-associated diseases, osteoarthritis, osteoporosis, asthma, chronic obstructive pulmonary disease (COPD), periodontitis, atherosclerosis, psoriasis, corneal, its lower homologue. Again, the substantial increase in oral bioavailability from 14% to 90% is far more than could have been expected.

Compound 11 which is a cyclic 2-aminocarbamoylphosphonate, may be compared to its analogous acyclic 2-aminocarbamoylphosphonate, compound 6. From such comparison we may note that compound 11 is about 13 times more active in vitro on MMP-2 than its acyclic analog, 6. Compound 11 also shows selective in vivo activity against restenosis.

TABLE 1

| No. | Structure | Chemoinvasion % inhibition at 50 μM | MMP-2 IC50 μM | MMP-9 IC50 μM | Capillary Formation Inhibition % At 50 μM | In vivo murine melanoma iIp/po % reduction IP | PO |
|---|---|---|---|---|---|---|---|
| | | 1-7 Previously described compounds | | | | | |
| 1 | CyclopentylNHCOPO$_3$H$_2$ | 65 | 0.080 | >100 | 70 | 72 | 71 |
| 2 | CyclopentylNHCSPO$_3$H$_2$ | 70 | 0.07 | 50 | | 56 | 70 |
| 3 | CyclohexylNHCOPO$_3$H$_2$ | 46 | 3 | >100 | 50 | 64 | |
| 4 | CyclohexylNHCSPO$_3$H$_2$ | 50 | 0.10 | >100 | 38 | 68 | |
| 5 | CyclohexylCH$_2$NHCOPO$_3$H$_2$ | 50 | 0.2 | 1 | 53 | 69 | 14 |
| 6 | H$_2$N(CH$_2$)$_2$NHCOPO$_3$H$_2$ | 45 | 0.80 | 2 | 43 | 57 | |
| 7 | Me$_2$N(CH$_2$)$_2$NHCOPO$_3$H$_2$ | 66 | 0.030 | 20 | 75 | 75 | 29 |
| | | 8-11 Novel Compounds | | | | | |
| 8 | CyclohexylCH$_2$NHCSPO$_3$H$_2$ | 70 | 0.015 | 0.015 | 75 | 80 | 80 |
| 9 | (R)-Cyclohexyl-EtHCOPO$_3$H$_2$ | 33 | 0.20 | 100 | 35 | 68 | 90 |
| 10 | endo-2-NorbornylNHCOPO$_3$H$_2$ | 25 | 0.10 | >100 | 30 | 87 | 80 |
| 11 | cis-2-AminocyclohexylNHCOPO$_3$H$_2$ | 62 | 0.060 | 20 | 72 | 77 | 86 |

As regards the selectivity of the compounds of the present invention, Table 2 displays the IC$_{50}$ values of selected carbamoylphosphonates toward five subtypes of MMP enzymes. From Table 2 it is to be noted that the carbamoylphosphonates of the present invention are specific inhibitors of MMP-2, the most clinically important enzyme subtype compared to the four other MMP subtypes. This selectivity is a great benefit of the compounds of the invention.

The results in Table 2 also show the importance of the steric structure for activity and selectivity. Thus, the optical isomer 9 is five times more active than 9a, and far more selective against MMP-2 than against the other tested MMPs.

Similar comparison of the geometrical isomers 10 and 10a shows that the former is 150 times more active against MMP-2 and again 10 is more selective against MMP-2 than the exo compound 10a. The cis-aminocyclohexyl compound 11 is also 300 times more active against MMP-2 than its geometrical trans isomer, 11a, and the selectivity of 11 is also far greater than that of 11a.

The structures of the new compounds 9, 9a, 10, 10a, 11 and 11b, listed in Table 2 are as follows:

TABLE 2

Selectivity of carbamoylphosphonic acids 9-11 towards different MMPs:

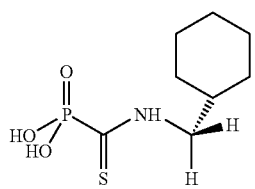

8
cyclohexylmethylthiocarbamoylphosphonic acid

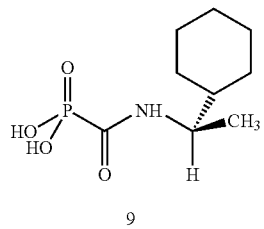

9
(R)-1-cyclohexylethylcarbamoylphosphonic acid

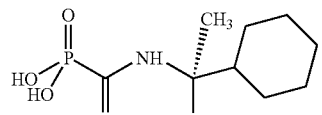

9a
(S)-1-cyclohexylethylcarbamoylphosphonic acid

TABLE 2-continued

Selectivity of carbamoylphosphonic acids 9-11 towards different MMPs:

10
endo-2-norbornylcarbamoylphosphonic
acid 10a
exo-2-norbornylcarbamoylphosphonic
acid 11
cis-2-aminocyclohexylcarbamoylphosphonic
acid 11a
trans-2-aminocyclohexylcarbamoylphosphonic
acid

| Symbol | Structure | MMP-1 $IC_{50}$ μM | MMP-2 $IC_{50}$ μM | MMP-3 $IC_{50}$ μM | MMP-8 $IC_{50}$ μM | MMP-9 $IC_{50}$ μM |
|---|---|---|---|---|---|---|
| 9 | (R)-cyclohex-Et NHCOPO$_3$H$_2$ | >100 | 0.20 | >100 | >100 | >100 |
| 9a | (S)-cyclohex-Et NHCOPO$_3$H$_2$ | 2 | 1 | 0.1 | >100 | 10 |
| 10 | endo-2-norborn NHCOPO$_3$H$_2$ | >100 | 0.10 | >100 | >100 | >100 |
| 10a | exo-2-norborn NHCOPO$_3$H$_2$ | 1 | 15 | >100 | >100 | >100 |
| 11 | (Z)-2-aminocychexyl NHCOPO$_3$H$_2$ | >100 | 0.06 | >100 | >100 | 20 |
| 11a | (E)-2-aminocyclohexylNHCOPO$_3$H$_2$ | 90 | 20 | 25 | 50 | >100 |

A compound of formula I may be administered per se or, preferably, as a pharmaceutical composition also comprising a pharmaceutically acceptable carrier. Accordingly, the present invention also provides a pharmaceutical composition comprising a compound of the general formula I, or a pharmaceutically acceptable salt thereof, or a pharmaceutically acceptable solvate thereof, and a pharmaceutically acceptable carrier.

As used herein the term "pharmaceutically acceptable" embraces compounds, compositions and ingredients for both human and veterinary use.

Usually the pharmaceutical compositions of the present invention will be adapted for oral administration, although compositions for administration by other routes, such as by injection and percutaneous absorption are also envisaged. Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant. Typical carriers include, for example, microcrystalline cellulose, starch, sodium starch glycollate, polyvinylpyrrolidone, polyvinylpolypyrrolidone, sodium lauryl sulphate or sucrose.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

The invention will now be illustrated by the following non-limiting examples.

EXAMPLES

A. Synthetic Procedures

Example 1

Diethyl
N-(cyclohexylmethyl)carbamoylphosphonate

A solution of triethyl phosphonothiolformate (1.28 g, 5.65 mMol) and cyclohexylmethylamine (0.75 ml, 5.76 mMol) in MeCN (10 ml) was kept at room temperature for 3 days. The volatiles were removed, to give 1.4 g residue (89.3%) of oily product. NMR (CDCl$_3$) $^{31}$P −2.01 ppm. $^1$H, 0.8-1.3 (m, 5H), 1.33 (t, J=6.9 Hz, 6H), 1.4-1.75 (m, 5H), 3.13 (t, J=6.9 Hz, 2H), 4.18 (m, 4H), 7.23 (m, 1H). Anal. Calcd. for C$_{12}$H$_{24}$NO$_4$P: C, 51.98; H, 8.72; N, 5.05. Found: C, 51.15; H, 9.14; N, 5.38.

Example 2

Diethyl
N-(cyclohexylmethyl)thiocarbamoylphosphonate

A solution of diethyl N-cyclohexylmethylcarbamoylphosphonate (2.3 g, 8.3 mMol) and Lawesson reagent (1.68 g, 4.1 mMol) in toluene (60 ml) was refluxed for 1 h. $^{31}$P NMR indicated disappearance of the starting material and the appearance of a new peak at −1.93 ppm accompanied with some impurities. The solvent was evaporated and the residue was purified by chromatography over silica gel. The desired product was eluted by AcOEt to yield 0.62 g pure product as yellow crystals, m.p. 53° C. (from acetone-hexane). NMR (CDCl$_3$) $^{31}$P, −1.34 ppm. $^1$H, 9.03 (1H bs); 4.31-4.13 (4H m); 3.53 (2H, t J=5.7 Hz); 1.75-1.65 (5H, m); 1.35 (6H t) 1.44-0.95 (6H, m). Anal. Calcd. for C$_{12}$H$_{24}$NO$_3$PS: C, 49.14; H, 8.19; N, 4.77. Found: C, 49.45; H, 8.38; N, 4.60.

Example 3

N-(Cyclohexylmethyl)thiocarbamoylphosphonic acid (8)

A solution of diethyl N-cyclohexylmethylthiocarbamoylphosphonate (0.6 g) and bromotrimethylsilane (1.08 ml) in acetonitrile (15 ml) was kept overnight at ambient temperature. The reaction mixture was decomposed by methanol and evaporated to dryness to give 0.45 g semisolid. NMR (D$_2$O ) $^{31}$P, −0.48 ppm. $^1$H, 3.39 (2H, dd, $^3J_{HH}$=7.2 Hz, $^4J_{HP}$=1.6 Hz); 1.6-1.4 (5H, m); 1.15-0.8 (6H, m).

Example 4

Diethyl N—[(R)-1-Cyclohexylethyl]carbamoylphosphonate

A solution of triethyl phosphonothiolformate (2.33 g, 10.31 mMol) and (R)-(−)-1-cyclohexylethylamine (1.56 ml, 10.52 mMol) in MeCN (15 ml) was kept at room temperature overnight. The solvent was evaporated in vacuo and the residue was dried in high vacuum to remove traces of solvent to leave 2.84 g, 94.6% product. NMR (CDCl$_3$) $^{31}$P −0.78 ppm. $^1$H 0.80-1.80 (m's, 11H), 1.08 (d superimposed, J=6.9 Hz, 3H), 1.32 (t super imposed, J=7.2 Hz, 6H), 3.90 (m, 1H), 4.17 (m, 4H), 6.90 (brd, 1H).

Example 5

N—[(R)-1-Cyclohexylethyl]carbamoylphosphonic acid (9)

A solution of diethyl N—[(R)-1-cyclohexylethyl]carbamoylphosphonate (2.368 g, 8.12 mmol) and TMSBr (5.26 ml, 40.62 mMol) in MeCN (15 ml) was kept at room temperature for 2.5 h. The solvent was evaporated, MeOH (10 ml) was added and evaporated. The solid residue (1.884 g, 98%) was recrystallized from EtOH, m. p. 155-156° C., [α]$_D$=+ 20.98 (c=0.07 MeOH). NMR (D$_2$O) $^{31}$P −2.60 ppm. $^1$H, 0.60-1.56 (m's, 11H, cyclohexyl), 0.94 (d superimposed, J=6.9 Hz, 3H, CHCH$_3$), 3.56 (quin, J=6.9 Hz, 1H, NHCH). Anal. Calcd. for C$_9$H$_{18}$NO$_4$P: C, 45.96; H, 7.66; N, 5.96. Found: C, 45.69; H, 7.55; N, 5.66.

Example 6

N—(S)-(−)-1-Cyclohexylethyl)carbamoylphosphonic acid (9a)

a) Diethyl N—[(S)-(+)-1-Cyclohexylethyl]carbamoylphosphonate

A solution of triethyl phosphonothiolformate (2.38 g, 10.53 mMol) and (S)-(+)-1-cyclohexylethylamine (1.6 ml, 10.76 mMol) in MeCN (15 ml) was kept at room temperature overnight. The volatiles were removed, and the residue was dried in high vacuum to yield 2.35 g colorless oil, (76%). NMR (CDCl$_3$) 31P −0.78 ppm. 1H, 0.80-1.80 (m's, 11H, cyclohexyl), 1.10 (d super imposed, J=6.9 Hz, 3H, CHCH$_3$), 1.34 (t superimposed, J=7.2 Hz, 6H, 2×CH$_3$CH$_2$O), 3.90 (m, 1H, NHCH), 4.20 (m, 4H, 2×CH$_3$CH$_2$O), 6.86 (br. 1H, NH).

b) N—(S)-(−)-1-Cyclohexylethyl)carbamoylphosphonic acid (9a)

A solution of diethyl N—[(S)-(+)-1-cyclohexylethyl]carbamoylphosphonate 1.997 g, 6.85 mMol) and TMSBr (4.43 ml, 34.25 mMol) in MeCN (15 ml) was kept at room temperature for 2.5 h and evaporated. MeOH (10 ml) was added and evaporated leaving behind 1.61 g white solid (99%) m. p. 167-168° C., [α]$_D$=−20.21, (c=0.07, MeOH) NMR (D$_2$O) 31P −2.62 ppm. 1H 0.60-1.56 (m's, 11H, cyclohexyl), 0.90 (d superimposed, J=6.9 Hz, 3H, CHCH$_3$), 3.52 (quin, J=6.9 Hz, 1H, NHCH). Anal. Calcd. for C$_9$H$_{18}$NO$_4$P: C, 45.96; H, 7.66; N, 5.96. Found: C, 46.09; H, 7.66; N, 5.79.

Example 7

Diethyl N-[endo-2-norbornyl]carbamoylphosphonate

To endo-2-aminonorbornane hydrochloride (1 g, 6.77 mMol) dissolved in DMF (10 ml) was added Et$_3$N (0.94 ml, 6.77 mMol) causing the precipitation of Et$_3$NH$^+$ Cl$^-$. To the reaction mixture was added solution of triethyl phosphonothiolformate (1.53 g, 6.77 mMol) dissolved in (DMF 5 ml) and the reaction mixture was stirred at room temperature for 3 days. The solvent was evaporated in vacuo, and the residue was dissolved in ether and extracted with HCl 5% and water. After drying and evaporation of the ether a white solid was obtained, 1.494 g, (80%), m. p. 48-50° C. NMR (CDCl$_3$) $^{31}$P −1.13 ppm. $^1$H 0.82 (dt, J=13.5, 4.5 Hz, 1H), 1.10-1.65 (m, 12H), 2.06 (tt, J=13.5, 4.5 Hz, 1H), 2.22 (t, 1H), 2.45 (s, 1H), 4.10-4.25 (m, 5H), 7.05 (brd, (1H). Anal. Calcd. for C$_{12}$H$_{22}$NO$_4$P: C, 52.28; H, 7.98; N, 5.08. Found: C, 52.01; H, 7.85; N, 5.32.

Example 8

N-[endo-2-norbornyl]carbamoylphosphonic acid (10)

A solution of diethyl N-endo-2-norbornylcarbamoylphosphonate (1.246 g, 4.52 mmol) and TMSBr (2.93 ml, 22.63 mMol) in MeCN (15 ml) was kept at room temperature for 3 h. The solvent was evaporated, MeOH (10 ml) was added and evaporated. The solid residue was recrystallized from EtOH, yield 0.727 g, 73%, m. p. 164-165° C. NMR (D$_2$O) $^{31}$P, −2.79 ppm. $^1$H, 0.76 (dt, J=13.2, 3.3 Hz, 1H), 1.0-1.4 (m's, 6H), 1.81 (m, 1H), 2.02 (s, 1H), 2.21 (s, 1H), 3.80 (brd, 1H). Anal. Calcd. for C$_8$H$_{14}$NO$_4$P: C, 43.83; H, 6.39; N, 6.39. Found: C, 43.79; H, 6.18; N, 6.19.

Example 9

N-[exo-2-norbornyl]carbamoylphosphonic acid (10a)

a) Diethyl [exo-2-norbornyl]carbamoylphosphonate

A solution of triethyl phosphonothiolformate (1.96 g, 8.66 mMol) and exo-2-aminonorbornane (1 g, 8.99 mMol) in MeCN (15 ml) was kept at room temperature overnight. The volatiles were evaporated, and the residue dried in high vacuum to give an oil, 2.28 g (95%). NMR (CDCl$_3$) 31P, −1.09 ppm. 1H, 1.00-1.50 (m's, 13H), 1.75 (m, 1H), 2.18 (d, J=3.3 Hz, 1H), 2.24 (s, 1H), 3.74 (m, 1H, NHCH), 4.10-4.25 (m, 4H, 2×CH$_3$CH$_2$O), 6.97 (brd, (1H, NH).

b N-[exo-2-norbornyl]carbamoylphosphonic acid (10a)

A solution of diethyl N-exo-2-norbornylcarbamoylphosphonate (1.46 g, 5.3 mmol) and TMSBr (3.42 ml, 26.45 mMol) in MeCN (15 ml) was kept at room temperature for 4 h. The solvent was evaporated, MeOH (10 ml) was added and evaporated. The solid residue was recrystallized from EtOH, (1 g, 86%) m. p. 170-172° C. NMR (D$_2$O) 31P −2.79 ppm. 1H, 0.85-1.05 (m's, 3H), 1.05-1.47 (m, 4H), 1.50-1.60 (m, 1H), 1.98 (d, J=3 Hz, 1H), 2.07 (s, 1H), 3.41 (brd, 1H, NHCH). Anal. Calcd. for C$_8$H$_{14}$NO$_4$P. C, 43.83; H, 6.39; N, 6.39. Found: C, 43.87; H, 6.67; N, 6.22.

Example 10

Diethyl N-(cis-2-aminocyclohexyl)carbamoylphosphonate

To a solution of cis-1,2-diaminocyclohexane (1 g, 8.75 mMol) in MeCN (15 ml) was added dropwise triethyl phosphonothiolformate (2 g, 8.8 mMol) dissolved in MeCN (15 ml) over a period of about 10 min, and the reaction mixture was stirred at room temperature for an additional period of 1.5 h. Examination of the reaction mixture by $^{31}$P NMR showed two signals: 1) at 0.19 ppm (83.5%) corresponding to the monophosphonoformylation product, and 2) at −0.59 ppm (16.5%), corresponding to the bisphosphonoformylation product. After evaporation of the solvent the crude reaction mixture was subjected to reaction with "Boc-anhydride" in order to separate the products.

Example 11

Diethyl N-(cis-2-Boc-aminocyclohexyl)carbamoylphosphonate

To the product of Example 8 dissolved in EtOH was added "Boc-anhydride" (3.5 g, 16 mMol) and the reaction mixture was stirred for 2.5 h at room temperature. Examination of the reaction mixture by $^{31}$P nmr showed two signals: 1) at −38 ppm (83.5%) and 2) at −0.65 ppm (16.5%). The solvent was removed in vacuo and the residue was separated by chromatography (AcOEt/Pet. Ether, 85:15) to give 2.36 g of the monophosphorylated product (Rf=0.6), m. p.>240° C. NMR (CDCl$_3$) $^{31}$P −1.19 ppm. $^1$H, 1.30-1.85 (m, 23H), 3.92 (m, 1H), 4.10-4.30 (m, 5H), 4.80 (brd, J=6.9 Hz), 7.42 (br s, 1H).

Example 12

N-(cis-2-aminocyclohexyl)carbamoylphosphonic acid (11)

A solution of diethyl N-(cis-2-Boc-aminocyclohexyl)carbamoylphosphonate (2.36 g, 6.25 mMol) and TMSBr 4.85 ml, 37.5 mMol) in dry dioxane (20 ml) was stirred at 60° C. for 3 h. Examination of the reaction mixture by $^{31}$P NMR revealed the presence of two signals, 1) at −17.2 ppm, (48%) corresponding to the bis-de-ethylated product still having the "Boc" group in the molecule, and 2) at −19.5 ppm, (42%) corresponding to the completely deprotected compound. After two weeks at room temperature the solution contained only the second compound. The volatiles were evaporated, the residue was treated with MeOH (10 ml) and evaporated again, to give a white solid. The product was washed with EtOH and dried, m.p. 248-250° C. NMR (D$_2$O), $^{31}$P −2.21 ppm. $^1$H, 1.20-1.75 (m, 8H), 3.35 (m, 1H), 4.24 (m, 1H). Anal. Calcd. for C$_7$H$_{15}$N$_2$O$_4$P: C, 37.84; H, 6.75; N, 12.61. Found: C, 37.48; H, 6.49; N, 12.36.

Alternatively, compound 11 was also prepared from diethyl N-(cis-2-Boc-aminocyclohexyl)carbamoylphosphonate by room temperature treatment with trifluoroacetic acid to remove the "Boc" protecting group, to yield diethyl N-(cis-2-aminocyclohexyl)carbamoylphosphonate followed by bromotrimethylsilane mediated dealkylation at room temperature. Although, in contrast to the previously described one-pot method, this consists of two steps, it can be completed in less time.

Example 13

Trans-2-aminocyclohexylcarbamoyl phosphonic acid (11a)

a) Diethyl N-(trans-2-aminocyclohexyl)carbamoylphosphonate

To a solution of trans-1,2-diaminocyclohexane (0.53 ml, 4.41 mMol) in MeCN (5 ml) was added dropwise over a period of 10 minutes, triethyl phosphonothiolformate (1 g, 4.41 mMol) dissolved in MeCN (5 ml). The reaction mixture was stirred at room temperature for 24 h. Examination by 31P nmr spectroscopy revealed the presence of two peaks at −0.764 and −0.171 ppm in the integration ratio of 72:28, indicating products. The major peak was assumed to belong to the product of bis-phosphonoformylation. In order to separate the products the reaction mixture was treated with "Boc-anhydride" as described below.

b) Diethyl N-(trans-2-[Boc-amino]cyclohexyl)carbamoylphosphonate

To the product of the previous step dissolved in EtOH was added "Boc-anhydride" (1 g, 4.58 mMol) and the reaction mixture was stirred overnight at room temperature. The solvent was removed in vacuo and the residue was separated by chromatography (AcOEt/Pet. Ether, 8:2) to give 0.42 g of the monophosphorylated product (Rf=0.48), m. p.>240° C. NMR (CDCl$_3$) 31P −1.61 ppm. 1H, 1.1-1.5 (m, 19H, cyclohex+Boc+2×CH$_3$CH$_2$O), 1.72 (m, 2H, cyclohex), 2.04 (m, 2H, cyclohex), 3.4 (m, 1H, CHNHBoc), 3.7 (m, 1H, CHNHCO), 4.2 (m, 4H, 2×CH$_3$CH$_2$O), 4.7 (d, J=6.9 Hz, 1H, NHBoc), 7.42 (br d, J=6.9 Hz, 1H, NHCO). Anal. Calcd. for C$_{16}$H$_{31}$N$_2$O$_5$P: C, 50.80; H, 8.20, N, 7.40. Found: C, 50.88; H, 8.17; N, 7.25.

After elution of the first product the column was developed by AcOEt/MeOH, 9:1, which eluted a second product that resulted from bisphosphorylation, 0.223 g, Rf=0.1, m. p. 150-152° C. Anal. Calcd. for C$_{16}$H$_{32}$N$_2$O$_8$P$_2$: C, 43.44; H, 7.24; N, 6.33. Found: C, 43.26; H, 7.30; N, 6.14.

c) (N-(trans-2-aminocyclohexyl)carbamoylphosphonic acid (11a)

A solution of diethyl N-(trans-2-B-aminocyclohexyl)carbamoylphosphonate (0.4 g, 1.06 mMol) and TMSBr (0.8 ml, 6.18 mMol) in dry dioxan (10 ml) was stirred under reflux for 3 h and at room temperature overnight. The solvent was evaporated, MeOH (10 ml) was added and evaporated again to yield a light brown solid, which was recrystallized from EtOH). 18 g, 76%, m. p.>240° C. NMR (D$_2$O) 31P −3.15 ppm. 1H, 1.0-2.0 (m's, 8H, cyclohex), 3.04 (td, J=11.7, 3.9 Hz, 1H, CHNH$_2$), 3.77 (td, J=11.7, 3.9 Hz, 1H, CHNHCO). Anal. Calcd. for C$_7$H$_{15}$N$_2$O$_4$P, C, 37.84; H, 6.75; N, 12.61. Found: C, 37.18; H, 6.75; N, 11.96.

B. Biological Studies

The biological effects, summarized in Table 1 above, were evaluated in the following models.

Matrigel Chemoinvasion Assay

This assay measures in vitro the potency of the compounds to repress the invasiveness of cancer cells, by inhibiting the MMPs produced by them. The assay uses a reconstituted basement membrane preparation, which is similar to the natural basement membranes that the tumor cells have to cross, in order to disseminate. The compounds examined have been added to the invasion chambers at various concentrations, and the resulted invasion was compared to untreated preparations.

Description of the of the Matrigel Chemoinvasion Experiment a) The chemoinvasion assays were performed in Boyden chambers. Matrigel (25 µg) was dried on a polycarbonated filter (PVP free, Nucleopore). Fibroblast conditioned medium (obtained from confluent NIH-3T3 cells cultured in serum free DMEM) is used as the chemoattractant. Cells were harvested by brief exposure to 1 mM EDTA, washed with DMEM containing 0.1% bovine serum albumin and added to the Boyden chamber (200,000 cells). The chambers were incubated in a humidified incubator at 37° C. in 5% $CO_2$/95% air atmosphere for 6 h. The cells, which traversed the Matrigel layer and attached to the lower surface of the filter, were stained with Diff Quick (American Scientific Products) and counted.

The various compounds were examined as potential inhibitors at three concentrations: 100 µM, 50 µM and 10 µM. Compounds that were inactive at 100 µM were classified as inactive. The results (expressed in percents) that were obtained at 50 µM are listed in Table 1.

Determination of MMP Inhibitory Potency ($IC_{50}$ Values) in vitro

The commercially available recombinant MMP-2 and MMP-9 enzymes were incubated with succinylated-gelatin at four different concentrations for 3 h. The examined compounds were added at four to six different concentrations to the recombinant enzymes and the inhibitory potencies were expressed in a colorimetric change measured by an ELISA reader. The inhibitory activity ($IC_{50}$) was calculated from the kinetic data obtained.

Endothelial Cell Capillary Tube Formation

Some of the compounds were examined as to their potency to inhibit capillary formation, which is an in vitro model of angiogenesis, an essential step in the development of primary tumor and metastatic lesions. Endothelial cell migration to the newly formed tumor is the initial phase of angiogenesis, and is dependent on MMP expression. By using this assay that measures endothelial cell tube formation, the effects of some carbamoylphosphonates on angiogenesis at concentrations ranging from 100-5 µM were evaluated. Table 1, shows the results obtained from testing these carbamoylphosphonates at 50 micromolar concentration.

Description of the Endothelial Cell Capillary Tube Formation Experiment

Endothelial cells are harvested by 1 mM EDTA, and added to a Matrigel layer in a 24 well plate at 50,000 cells per well. After attachment, culture media (1 ml) is added and the plate is incubated as a monolayer culture. The plates are analyzed hourly using Hoffinan optics. This assay is used to evaluate inhibitory factors or stimulatory factors on capillary like structure formation, which may be added into the culture media.

Tumor Growth and Metastasis in Animal Models—in vivo Test

The abilities of the novel carbamoylphosphonates to inhibit the formation of metastatic lesions in vivo were examined in the murine melanoma model both by intraperitoneal (IP) and peroral (PO) administration. In this model, tumor cells were injected into the tail veins of mice, which were then treated by administering 50 mg/kg daily doses of the compounds examined for 21 days, and then the tumors formed on the lungs of the mice were counted after appropriate fixation. Each of the four compounds 8-11 was administered either by intraperitoneal injections or by the oral route to groups of 8 mice each. The results are listed in the Table 1. From these results it can be seen that the novel carbamoylphosphonates are endowed with greatly improved oral bioavailability. This is especially important, since oral administration is the most convenient one for the patient, especially for long term chronic treatments such as those envisaged for drugs that are the subject of this application.

Determination of Acute in vivo Toxicity of Representative Carbamoylphosphonates

Figure 2:
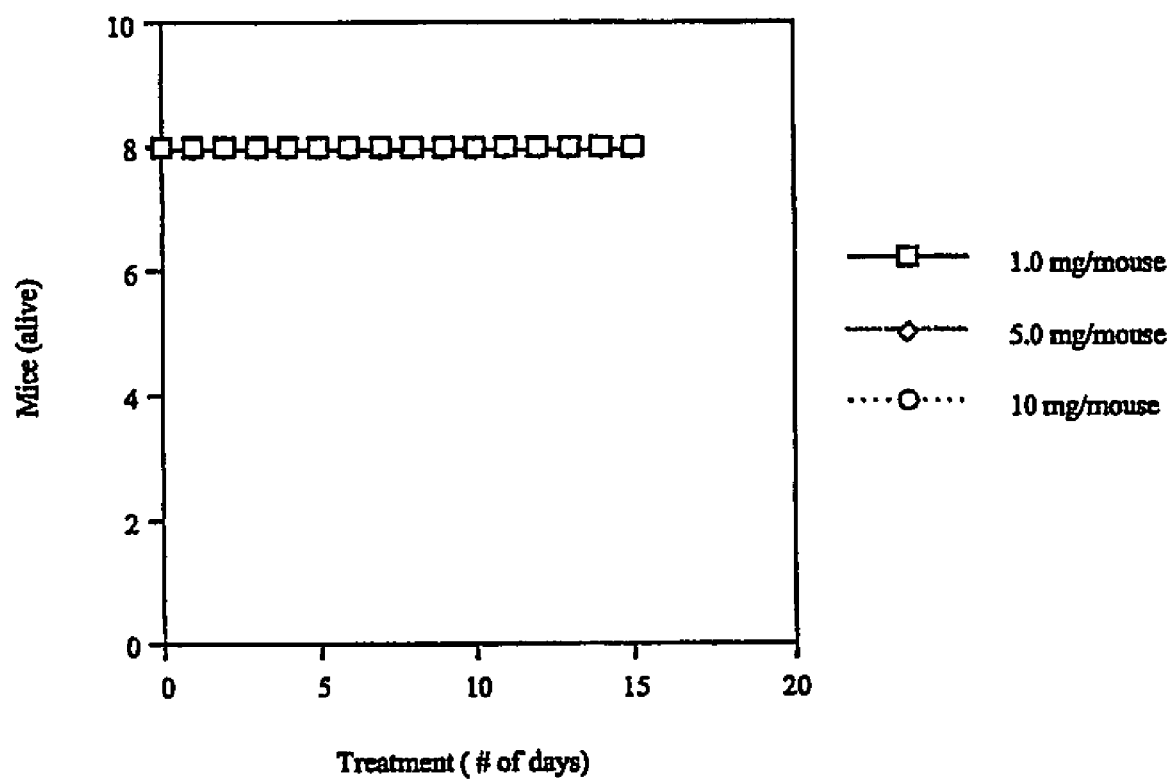
FIG. 2 is a graph showing the toxicity of compound 11 in mice at the same three doses as in FIG. 1.

Compounds 1 and 11 were administered to healthy mice daily for two weeks in three doses: 50 mg/kg, 250 mg/kg and 500 mg/kg, to groups of 8 mice each. The toxicity results relating to compound 1 are depicted in FIG. 1 while the toxicity results relating to the new compound 11 are depicted in FIG. 2. From these figures it is apparent that the cyclopentyl derivative, 1 is toxic at 250 mg/kg and 500 mg/kg doses while the 2-aminocyclohexyl derivative 11, is devoid of any toxicity even at 10 times the effective dose, namely at 500 mg/kg.

Rabbit Model of Restenosis

New Zealand White rabbits (Harlan Laboratories, Jerusalem, Israel) weighing 2.5 to 3.5 kg were used in accordance with the guidelines for animal care of the Hebrew University of Jerusalem and National Institutes of Health (USA). Animals were fed an atherogenic diet of 2% cholesterol and 6% peanut oil, starting 30 days before angioplasty. Hypercholesterolemia was ascertained (plasma cholesterol: 1200 mg/dL). Animals were anesthetized by xylazine (7 mg/kg) and ketamine (40 mg/kg). Heparin (200 U/kg), atropine (0.05 mg), and norfloxacin nicotinate (70 mg) were given. Balloon injury was performed on the left common carotid artery with a 3-mm angioplasty balloon catheter (Cordis, 231-minute inflation at 8 atm.). Animals randomly assigned were given IP injections of compound 11, administered on days −1, +1, +4, +6 and +8 (total dose, 70 mg/kg). The control animals received saline. An investigator blinded to the type of experimental group performed the experiments. After euthanasia with pentothal, arteries were perfusion-fixed in situ with 150 mL of 4% formaldehyde solution (pH 7.4), processed for morphometric analysis, and stained with Verhoeff elastin staining, Mayer hematoxylin and eosin, and modified Movat pentachrome. Five animals were used in the experiment and five in the control group.

Figure 3:
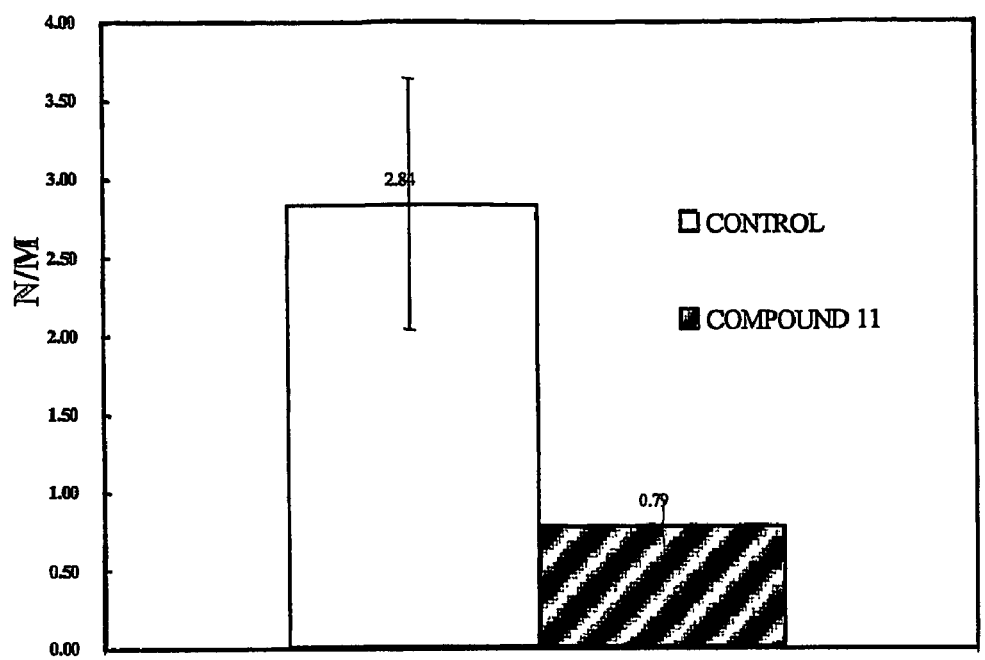
FIG. 3 presents the effect of compound 11 on the ratio of neointimal hyperplasia expressed as mean neointima-to-media area ratio (N/M).
Figure 4:
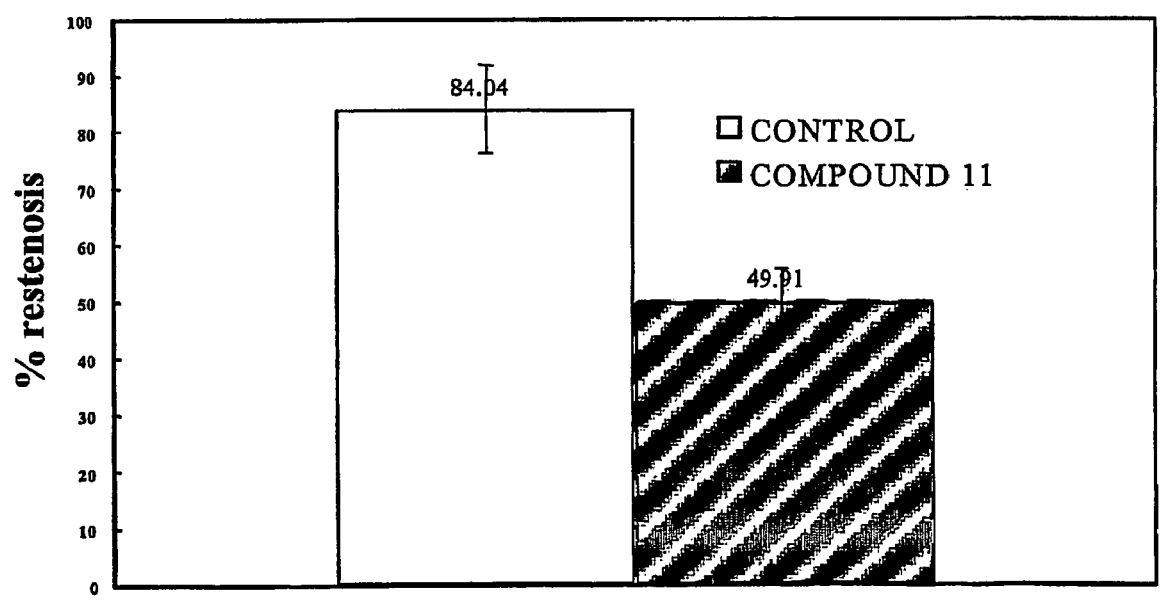
FIG. 4 presents the effect of compound 11 on % restenosis.

Results:

A significant and marked inhibition of restenosis was observed in the hypercholesterolemic rabbit model of restenosis after 30 days following intraperitoneal treatment with 70 mg/kg divided in 5 doses of cis-2-aminocyclohexylcarbamoylphosphonic acid, 11, over 8 days. These results are shown in FIGS. 3 and 4. More specifically, FIG. 3 shows the ratio between the newly formed intima and the thickness of the blood vessel wall of a control group vs. a group treated by compound 11. FIG. 4 shows the blocked cross section of the vessel of a control group vs. a group treated by compound 11.

Figures 5A, 5B:
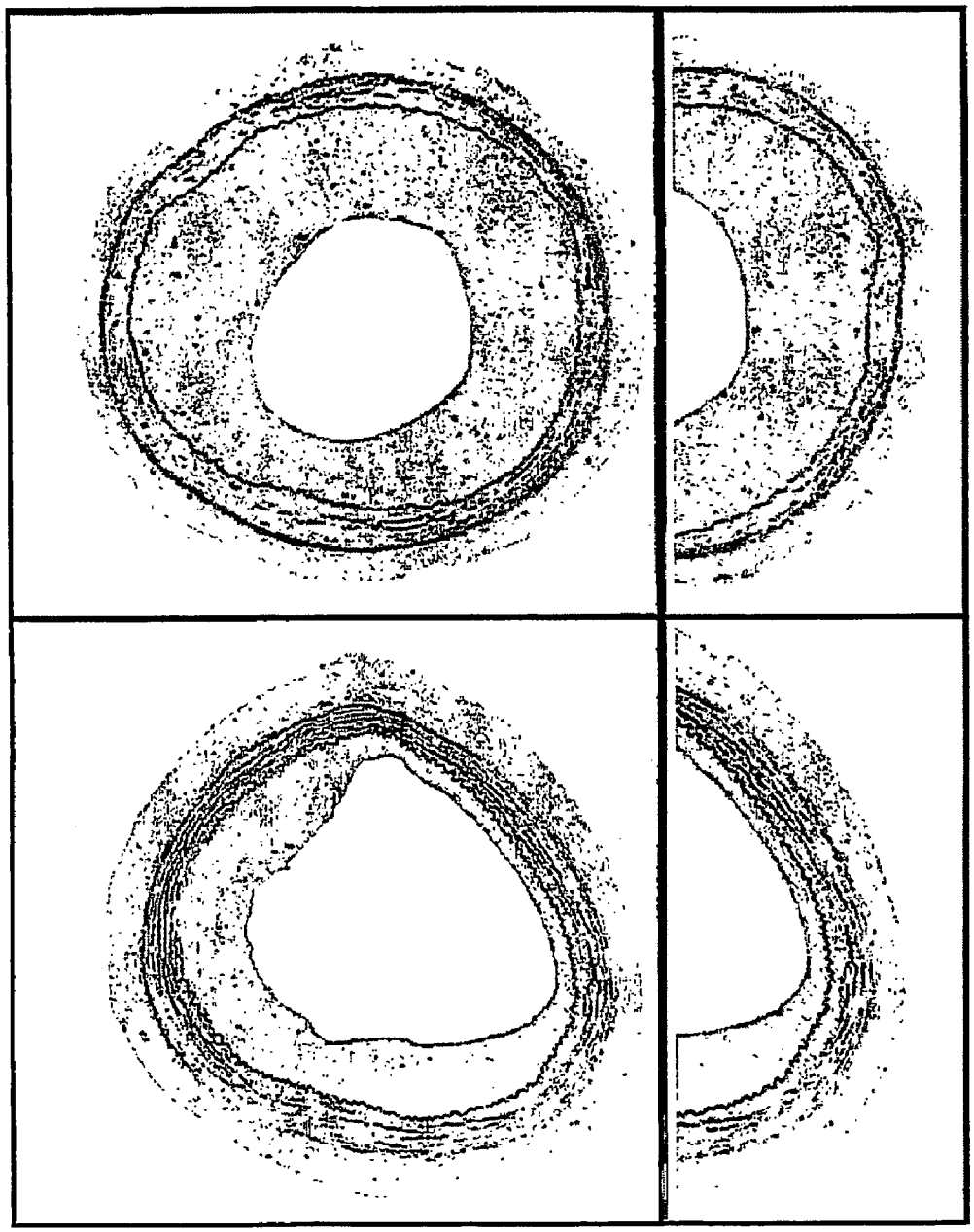
FIG. 5 shows the difference between treated (5A) and control (5B) rabbit carotid artery, where the treatment was initiated on day −1, and a dose of 70 mg of compound 11 divided into five doses, was administered on days −1, +1, +4, +6 and +8.

The marked inhibition of restenosis is unparalleled to other therapeutic modalities in this model (various antiinflammatories or antiproliferative agents). Moreover, restenosis treatment by known MMP inhibitors such as Batimastat failed in same model. It should be noted that the larger lumen in the treatment group was achieved despite the general smaller size of the artery. The histological picture of the blood vessel wall and the occluded area of the vessel, is showed in FIGS. 5A (group treated by compound 11) and 5B (untreated, control group). Thus, it is plausible to suggest that a lower dose would be also effective in reducing restenosis without affecting vessel size.

Without being bound to theory, it is suggested that the mode of action of the new compounds of the invention is via MMP inhibition and/or inhibition of angioneogenesis.

Prostate Tumor Model

Figure 6:
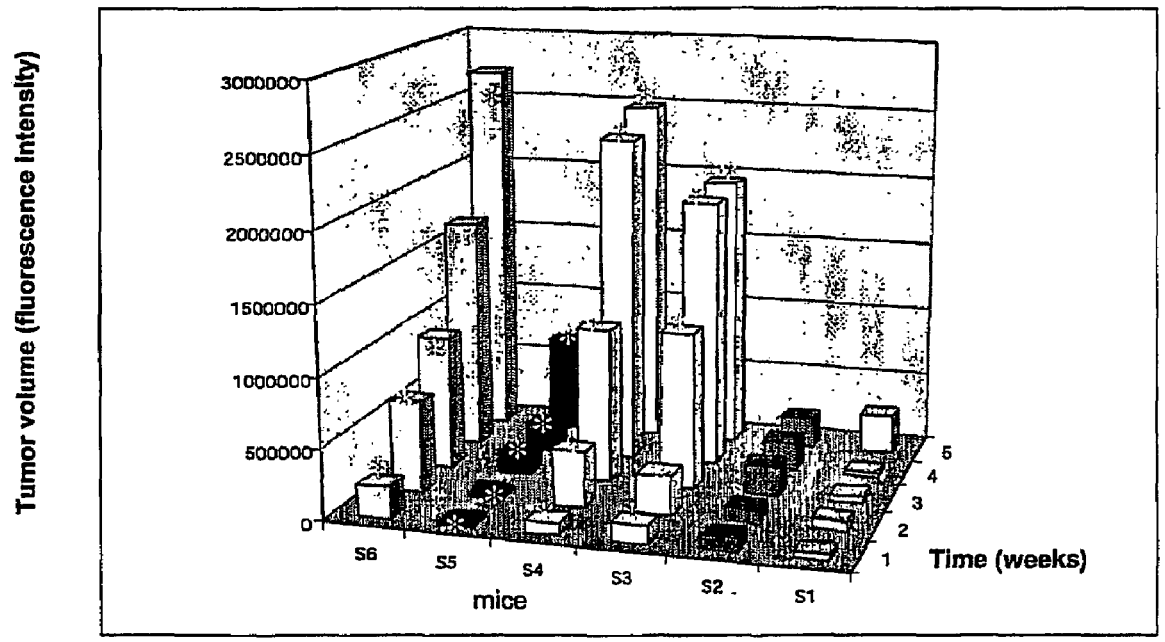
FIG. 6 shows the results of a control experiment of an orthotopic prostate cancer model, in which mice were monitored for 5 weeks without treatment.
Figure 7:
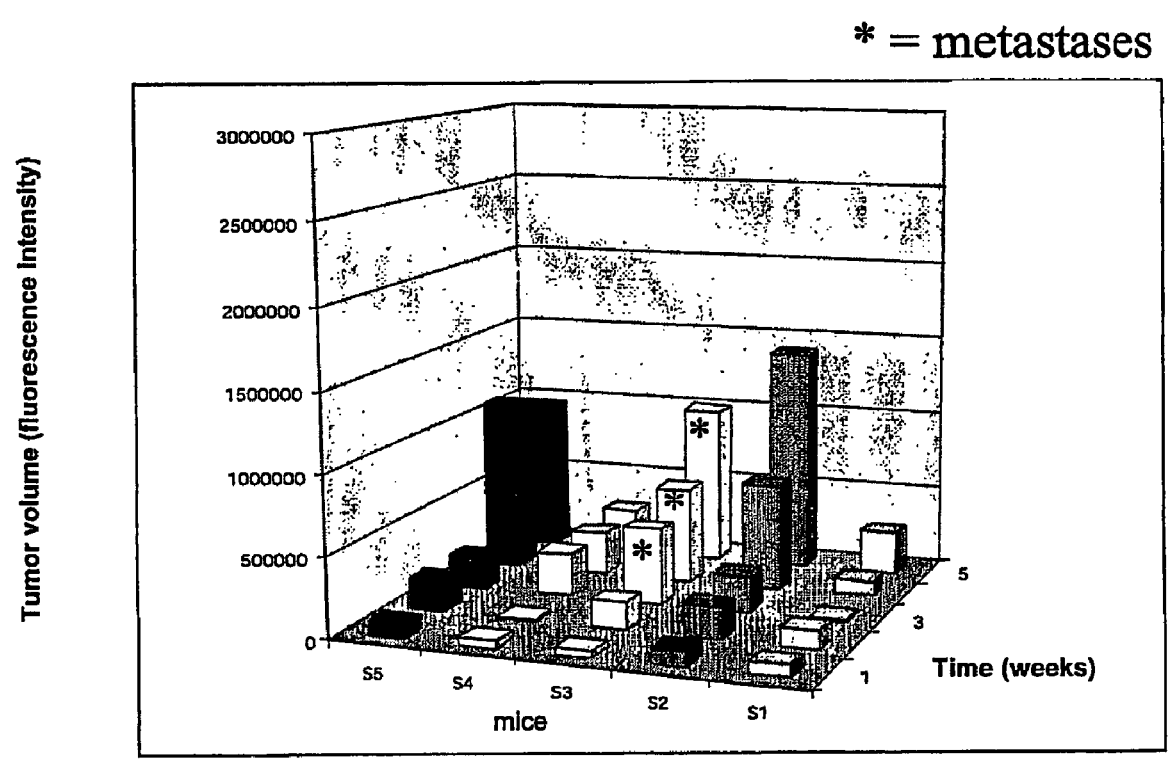
FIG. 7 shows the results obtained in a treated group in the orthotopic prostate cancer experiment, in which mice were treated by daily intraperitoneal injections of compound 11 for 5 weeks.

Human prostate tumor cells DU145, PC3 or LMCap transfected with a luciferase gene were injected orthotopically into the prostate of male mice ($2 \times 10^6$ cells/mouse). The experimental mice were treated daily with compound 11 (50 mg/kg IP). The mice were monitored for local tumor growth and metastasis formation with a cooled charged coupled device camera (CCCD) sensitive to photons, weekly, starting 14 days after tumor implantation. The emitted photons are converted into a digitalized image proportional to the amount of photons emitted by the tumor cell upon exposure to luciferin. FIG. 6 shows the results of a control experiment of an orthotopic prostate cancer model, in which mice were monitored for 5 weeks without treatment, while FIG. 7 shows the results obtained in a treated group in the orthotopic prostate cancer experiment, in which mice were treated by daily intraperitoneal injections of compound 11 for 5 weeks. As it may seen, mice treated with compound 11 show a significantly lower tumor volume and significantly lower tumor dissemination. Thus, the compound 11 inhibited the metastatic spread of the tumor and further, it also prevented the local tumor growth as evident from the smaller tumor volume in the treated mice.

What is claimed is:

1. A compound of formula 1 or a geometrical isomer or optically active form thereof:

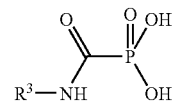

I a pharmaceutically acceptable salt, solvate, and hydrate of said compound or a geometrical isomer or an optically active form thereof, wherein:

$R^3$ is a substituted cyclohexyl having at least one of alkyl, amino, amidino and guanidine, provided that $R^3$ is not cyclohexylmethyl.

2. The compound according to claim 1, wherein said cyclohexyl is substituted by at least one amino group.

3. The compound according to claim 1, wherein $R^3$ is selected from cyclohexylethyl, norbornyl and 2-aminocyclohexyl.

4. The compound according to claim 1, wherein $R^3$ is selected from (R)-1-cyclohexylethyl, endo-2-norbornyl and cis-2-aminocyclohexyl.

5. The compound according to claim 1, selected from:
a. N-(1-cyclohexylethyl)carbamoylphosphonic acid;
b. N-(2-norbornyl)carbamoylphosphonic acid; and
c. N-(2-aminocyclohexyl)carbamoylphosphonic acid or an optically active form, a pharmaceutically acceptable salt, hydrate and solvate thereof.

6. N-(cis-2-aminocyclohexyl)carbamoylphosphonic acid and pharmaceutically acceptable salts, hydrates and solvates thereof.

7. A pharmaceutical composition comprising as an active ingredient a compound of formula I according to claim 1 and a pharmaceutically acceptable carrier.

\* \* \* \* \*